US007871421B2

(12) United States Patent
Woodley

(10) Patent No.: US 7,871,421 B2
(45) Date of Patent: Jan. 18, 2011

(54) THERAPEUTIC RING

(75) Inventor: John Vivian Woodley, 49 Thomas Drive, Chevron Island, Queensland, 4217 (AU)

(73) Assignee: John Vivian Woodley, Queensland (AU)

( * ) Notice: Subject to any disclaimer, the term of this patent is extended or adjusted under 35 U.S.C. 154(b) by 19 days.

(21) Appl. No.: 11/334,611

(22) Filed: Jan. 19, 2006

(65) Prior Publication Data

US 2006/0167493 A1 Jul. 27, 2006

Related U.S. Application Data

(63) Continuation-in-part of application No. 10/148,207, filed on Aug. 22, 2002, now abandoned.

(30) Foreign Application Priority Data

Dec. 10, 1999 (AU) .................................. 64467/99

(51) Int. Cl.
*A61B 17/00* (2006.01)

(52) U.S. Cl. ..................................................... 606/204

(58) Field of Classification Search ................. 606/204, 606/189; 63/15; 2/21

See application file for complete search history.

(56) References Cited

U.S. PATENT DOCUMENTS

| | | | | | |
|---|---|---|---|---|---|
| 2,014,122 | A | * | 9/1935 | Armstrong | 63/15 |
| 2,346,607 | A | * | 4/1944 | Raiman | 63/15 |
| 2,937,798 | A | * | 5/1960 | Morf | 224/176 |
| 3,923,064 | A | * | 12/1975 | Leupold | 606/189 |
| 4,122,852 | A | * | 10/1978 | Knetsch et al. | 606/204 |
| 5,662,679 | A | * | 9/1997 | Voss et al. | 606/204 |
| 5,792,175 | A | * | 8/1998 | Yoo | 606/204 |
| 6,238,413 | B1 | * | 5/2001 | Wexler | 606/204.15 |
| 2005/0049631 | A1 | * | 3/2005 | Carter-Smith et al. | 606/204 |

FOREIGN PATENT DOCUMENTS

DE 24 24 219 A1 11/1975

* cited by examiner

*Primary Examiner*—Melanie Tyson
(74) *Attorney, Agent, or Firm*—Stein McEwen, LLP

(57) ABSTRACT

A therapeutic ring to be worn on an outer finger. The therapeutic ring includes a ring band and a pair of projections, the pair spaced on the ring band and extending from an inner surface of the ring band to apply continuous pressure to opposed sides only of an arterial or meridian channel in the outer finger.

3 Claims, 1 Drawing Sheet

THERAPEUTIC RING

CROSS-REFERENCED APPLICATION

This application is a continuation-in-part of patent application Ser. No. 10/148,207, filed Aug. 22, 2002 (Abandoned).

TECHNICAL FIELD

The present invention relates to rings for therapeutic use.

BACKGROUND ART

Rings which are said to improve circulation in the fingers and those which accomplish or mimic acupuncture treatments are known.

U.S. Pat. No. 5,792,175 describes a ring which has serpentine connecting portions between parallel plates upon which a plurality of protuberances are formed on the inner sides of the plates the ring is said to promote the circulation of blood by acupressuring randomly selected positions of the fingers by means of the protuberances.

U.S. Pat. No. 4,122,852 is another example of a ring having internal protuberances for acupressuring randomly selected positions of the fingers.

The human body has a number of arterial channels linked to various organs of the body by collaterals which emerge from the main channels.

One such channel extends from the outer finger via the arm to and is communicable with organs such as the heart, small intestine, eyes, ears and to sinus regions via collaterals.

The application of pressure to the channel of the outer finger is known to have a therapeutic effect on various organs and regions of the body.

Casual therapeutic treatments making use of channels and collaterals are commonly administered using acupuncture and massage techniques.

How Acupoints were Discovered

When examining their patients, the ancient Chinese practitioners felt pulsation at arterial loci (pulsing points). They believed that this pulse was caused by a vital force, which they called Qi. The difference between life and death was due to the presence or absence of Qi and all parts of the body were connected by a Qi channel or vessel. These ancient doctors diagnosed by palpating the arterial loci (pulsing points) and then they needled these points to treat a disease. Since they could not feel the pulsation along the entire presumed Qi channel, they postulated lines of connection between the acupoints on the loci of arteries, thus making a visible map of the unseen parts of the channel. Different practitioners in different times and places evolved their own ways to connect together the acupoints which they had identified, and this gave rise to a variety of theories to explain the channels or meridians. Even today traditional Chinese medical doctors are trained to feel this arterial pulsation, though only on the radial artery proximal to the wrist. The pulsing points of arteries were the earliest acupoints.

The Origin of Channel or Meridian Theories

Early acupuncture theories were formed from empirical experience. For example, ancient doctors found that for treating pain or other symptoms of the genitals, lower abdomen, and lumbar areas, needling certain pulsing loci on the dorsum of the foot and medial part of the lower leg was more effective than anywhere else. Thus they drew lines to connect the effective needling points with the parts of the body that were most affected by the needling, making a visible representation of the channel which connected all the points together. In this example the arterial points on the dorsum, the medial leg, the genital area, the lumbar area, and up to the tongue were joined together and thus the "liver channel", or "liver meridian," was gradually formulated. The other eleven meridians that are used today evolved in a similar way.

The theory of meridians, or channels, became one fo the cornerstones of TCM. As there were many different ways to delineate the same channel there were soon many different theoretical explanations. In his reconstruction of the development of ancient acupuncture practice Professor Huang shows that the ancient Chinese used the same character "mai" (•) to represent both "channels" and "blood vessels". In most Western textbooks, the character "mai" has been translated as "meridian" or "channel". Even today, acupuncture practitioners must learn a large and complex map of Qi channels (meridians) and other medical principles that are based on the ancient *Yellow Emperor's Canon of Internal Medicine.*

No treatments or objects have been proposed which are designed to apply continuous pressure to the arterial channel in the outer finger.

It is according an object of the present invention to provide a therapeutic ring which is adapted to apply pressure to the channel in the outer finger on a continuous basis.

Further objects and advantages of the present invention will become apparent from the ensuing description which is given by way of example.

SUMMARY OF INVENTION

According to the present invention there is provided a therapeutic ring adapted to be worn on an outer finger, the therapeutic ring comprising: a ring band; and a plurality of projections extending from an inner surface of the ring band, wherein the projections are adapted to apply continuous pressure to an arterial or meridian channel in the outer finger.

The ring can have two spaced projections extending from the inner surface of the ring band.

The ring band can be discontinuous.

The projections can be dome-shaped.

The ring band can be formed from a metal.

The ring band can be moulded or other wise formed in a plastics material.

Two projections can be provided, the spacing between the projections results in pressure being applied to opposed sides of the arterial or meridian channel.

Unlike rings of a similar design, the anti-snore therapeutic ring has been created to work in a specific and accurate manner, based around principles of acupressure points and their associated meridian channels. Unlike similar rings, the anti-snore ring has not been designed to be worn on any finger and its purpose is not to increase blood flow to the fingers.

The design of this ring is based around applying pressure to acupressure points within the outer finger. These points are very specific and if the ring was to be applied to other fingers, it would not be effective. The application of pressure stimulates the meridian channel that these acupressure points lie along. According to principles of the Chinese Medicine, these meridian channels are an invisible network that run throughout the body and maintain the flow of energy or Qi. By applying pressure to these specific points in the outer finger, the meridian channel that controls the small intestine, heart, and ear/nose/throat is activated and the flow of Qi is restored.

BRIEF DESCRIPTION OF THE DRAWINGS

Aspects of the present invention will now be described with reference to the accompanying drawings in which.

DETAILED DESCRIPTION OF THE INVENTION

Figure 1:
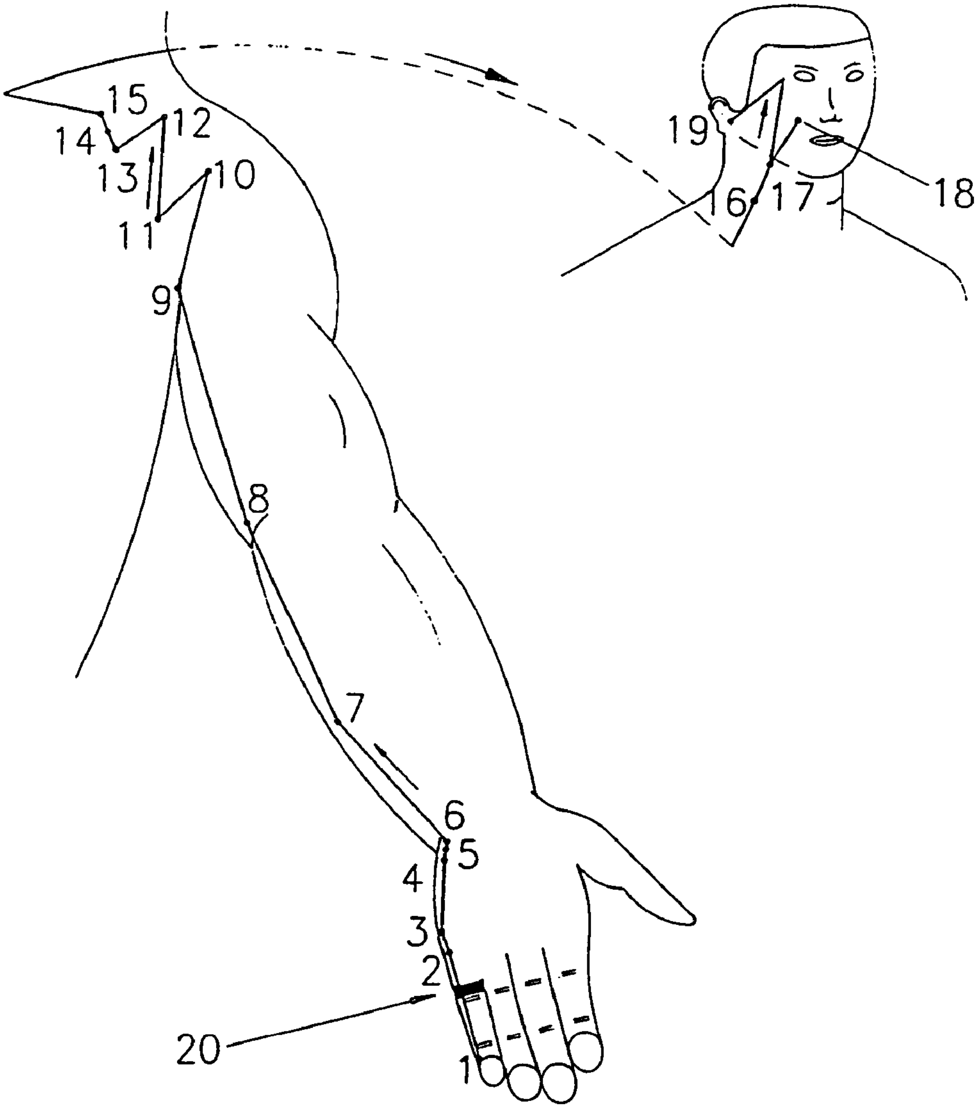
FIG. 1 is an illustration indicating the location of arterial or meridian channels and collaterals in the human body.

With respect to FIG. 1 of the drawings, in the human body a major arterial or median channel extends from the outer finger of the hand up the back of the arm to the neck region and branches off into the neck, sinus, eye and ears of a person.

The application of pressure to any of the points numbered 1 to 19 of the channels and collaterals will have varying beneficial affects.

The present invention provides a therapeutic ring generally indicated by arrow 20 which can be worn on a person's outer finger and applies pressure to the channel between points 1 and 2.

The ring applies pressure to the channel in the finger via projections extending from an inner surface thereof.

Figure 2:
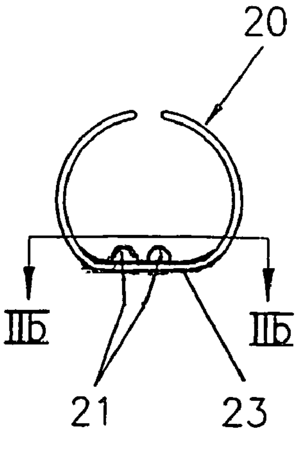
FIGS. 2, 2*a* and 2*b* are side plan and sectional views of a therapeutic ring in accordance with the present invention.
Figure 2A:
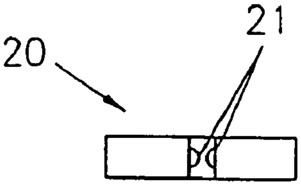
Figure 2B:
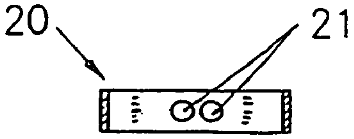

A ring in accordance with one possible embodiment of the present invention and as illustrated by FIGS. 2 to 2*b* can comprise a ring band indicated by arrow 20 having two projections 21 extending from the inner surface of the band.

The ring band 20 can be discontinuous having two spaced apart free ends.

The projections can be dome shaped as illustrated but other shapes are envisaged such as elongate strips or cross-shaped projections.

The ring can be produced in many materials but is by preference produced in metal which allows a fixed adjustment of the spacing between the free ends to be made for individual wearers.

The ring band 20 may be a regular semi-circle or a portion 23 of the ring band from which the projections 21 extend can be slightly flattened so that the projections are firmly applied in the arterial channel region of a person's finger.

The ring band is of a substantially rectilinear cross-section. Although the preferred construction of the ring is as described other alternative forms may be equally effective.

The ring band may be moulded in a resilient plastics material or be of a form similar to a tube or pipe strap with an adjustable tensioning device.

Aspects of the present invention have been described by way of example only and it will be appreciated that modifications and additions thereto may be made without departing from the scope thereof, as defined in the appended claims.

What is claimed is:

1. A therapeutic ring adapted to be worn on an outer finger of the human hand, the therapeutic ring consisting of:

a) a unitary discontinuous ring band having a pair of opposing spaced apart free ends, wherein said unitary discontinuous ring band and said pair of opposing spaced apart free ends of said ring band lie in a common plane, b) two projections extending inwardly from an inner surface of said ring band at a location diametrically opposite to the spaced apart free ends of said band, c) said projections spaced apart a distance sufficient to apply continuous pressure only on an arterial channel in the outer finger of the wearer.

2. The therapeutic ring as claimed in claim 1 wherein the projections are dome-shaped.

3. The therapeutic ring as claimed in claim 1, wherein said ring band is rectilinear in cross section.

* * * * *